United States Patent
Gielis et al.

(10) Patent No.: US 6,677,154 B2
(45) Date of Patent: Jan. 13, 2004

(54) MICROPROPAGATION, SYNTHETIC SEEDS AND GERMPLASM STORAGE OF BAMBOOS

(76) Inventors: Johan Gielis, Nottebohmstraat 8, B-2018 Antwerp (BE); John E. Woods, 144 County Rd. 575, Englewood, TN (US) 37329; Susan H. Woods, 144 County Rd. 575, Englewood, TN (US) 37329; Jan Oprins, St.-Lenaartsesteenweg 91, B-2310 Rijkevorsel (BE)

( * ) Notice: Subject to any disclaimer, the term of this patent is extended or adjusted under 35 U.S.C. 154(b) by 0 days.

(21) Appl. No.: 09/251,993

(22) Filed: Feb. 18, 1999

(65) Prior Publication Data

US 2002/0086425 A1 Jul. 4, 2002

(51) Int. Cl.$^7$ ............................ C12N 5/02; C12N 5/00; A01H 1/00; A01H 1/02; A01H 9/00
(52) U.S. Cl. ..................... 435/420; 435/430; 435/431; 435/410; 800/268; 800/260; 800/295; 800/298
(58) Field of Search ................................. 435/420, 430, 435/430.1, 431, 410; 800/268, 260, 295, 298

(56) References Cited

U.S. PATENT DOCUMENTS 5,334,530 A * 8/1994 Woods et al. .......... 435/240.48
5,427,593 A   6/1995 Carlson et al. .............. 47/57.6

FOREIGN PATENT DOCUMENTS

EP   WO 98/36635   *   8/1998

OTHER PUBLICATIONS

*Handbook of Plant Cell Culture*, vol. 1, "Techniques for Propagration and Breeding" Edited by D.A.Evans, W.R. Sharp, P.V. Ammirato, Y. Yamada.

* cited by examiner

Primary Examiner—Anne Marie Grunberg
(74) Attorney, Agent, or Firm—Parker & DeStefano; Kimberly O. Snead; Sheldon H. Parker

(57) ABSTRACT

The invention consists of several novel solutions to overcome specific problems currently encountered in propagating bamboo. The invention consists of these novel solutions both individually and in combination. The problem areas addressed by the various aspects of the invention include the following: a) Specific preparation of plants under stage 0 conditions, b) Use of diseased parts of bamboos as explants for initiation, c) Reversion of in vivo flowering in vitro, d) Subculture of flowering parts in vitro as monocultures, e) Induction of nodule cultures in monocultures of flowering parts, f) Induction of flowering in vitro by specific combination of chemical and physical parameters, g) Induction of somatic embryogenesis in adult bamboos without prior organogenesis, h) Production of synthetic seeds, i) Dehydration of somatic embryos prior to the production of synthetic seeds, j) Use of somatic embryos for cryopreservation using an encapsulation dehydration method, k) Use of bottomcooling and increased light intensity prior to transplantation, l) Use of micropropagated plants as micro-motherplants for further multiplication, and m) use of an acetone rinse for sterilization. The invention teaches how to begin with seeds, vegetative mature seedlings or inflorescences and efficiently micropropagate these on a large or mass scale. A variety of conditions including type of medium, concentrations of auxin and cytokinins, temperature, lighting, humidity and sterilization are disclosed, the use of which results in a high percentage success rate of micropropagation thereby allowing economically viable production of bamboo on a large or mass scale.

34 Claims, 2 Drawing Sheets

MICROPROPAGATION, SYNTHETIC SEEDS AND GERMPLASM STORAGE OF BAMBOOS

BACKGROUND OF THE INVENTION

The subfamily Bambusoideae (Poaceae) comprises both woody and herbaceous bamboos, but only woody bamboos have economic potential. At present about 120 genera of temperate and tropical woody bamboos are recognized, which are distributed worldwide covering 18 million hectares (ha), mainly in South East Asia, with about 3.8 million hectares in China and 8 million ha (13.8% of the forest land) in India.

Bamboos are versatile plants with many different applications. It has been estimated that about 2.2 billion people worldwide use bamboo more or less frequently and in 1985 the global revenue of bamboo was estimated around U.S. $4.5 billion. But bamboo also has a great future potential, since the use of bamboo as a raw industrial material is becoming more and more important and an increasing number of products are exported. Europe and North America import a lot of bamboo material from Asia such as toothpicks, sate sticks, brooms, poles for viticulture and arboriculture, small bamboo sticks for the production of ornamental plants and vegetables. Moreover bamboo parquet, new laminated products and other wood industry products, as well as exotic furniture, and a variety of handicraft items are found on the retail market.

The demand for bamboos will be exceedingly high, mainly due to serious forest depletion and the possibilities of using bamboo as a substitute for tropical timber. Currently the existing propagation techniques are clearly insufficient to meet the projected demands. While many classical techniques, such as clump division and cutting, are widely practiced, both their capacity to produce mass scale production, and their practical efficiency, are far too low. For example, to produce cutting, complete culms can be buried below soil level for some species. The rate of success is typically only 50% and for the production of 100,000 plants 10 hectares are needed.

The search for one single method for large scale production for all bamboos remains thus highly desirable. Micropropagation is an excellent method to achieve this aim. In a short period of time large numbers of bamboos can be produced in the laboratory, starting from elite selected genotypes, which can be transported by air easily to any place in the world. Moreover tissue cultured plants are generally very vigorous growers and disease free.

Within micropropagation it is necessary to distinguish between large scale production and mass scale production. Large scale production typically ranges between 10,000 and 1 million plants per species per annum. A production of this size suffices for production as ornamental or for reforestation programs of the order of 2000 hectares. Especially in ornamental production and in pilot scale plantation, the added value is sufficiently high to use the method of axillary branching in vitro. This method has the additional advantages that of all possible methods for micropropagation, it has the lowest chance for genetic aberration, which certainly is of prime importance for ornamental production and pilot scale plantations, with feedback times for genotypic identity of 5–10 years at minimum.

Mass scale production on the other hand, aims at producing bamboos at the mass scales demanded by reforestation schemes. Magnitudes are in the order of 10–100 million plants per annum. The production of propagules for field planting and establishment has to be very cost-effective (read prices are very low) and the propagules cannot be handled and planted individually. The micropropagation method of choice here is somatic embryogenesis and encapsulation of these embryos into synthetic seeds. This allows the actual seeding of millions of plants.

Research papers have been published both on axillary branching and somatic embryogenesis of bamboo, but transforming the published protocols into practical economic propagation has been successful in only a very limited number of cases. Although there is published literature concerning tissue culture of bamboo, each paper tends to present a method applicable to only a single species. In the United States, at present all commercial bamboo is from vegetative culture and not from tissue culture.

The present proposal presents an invention which allows one to micropropagate any type of bamboo at both large and mass scale. It circumvents the problems encountered in research papers and in transforming research protocols into economically viable propagation systems. The economic viability of micropropagation systems is based on the large or mass scale production of high quality plants.

The added value of the tissue culture process can be maximized by using elite planting material that is selected on the basis of well defined selection criteria. Given the long feedback time for evaluation of genotypes and the location of the laboratory in relation to the habitat of the genotype (which may be several 1000 km apart), it is advisable to develop suitable storage methods. The suitability of tissue culture plants or propagules, provides excellent material for low temperature storage or cryopreservation. In this invention these methods are included as well.

The difficulties of propagation as currently practiced will be outlined followed by a description of the invention including a schematic diagram explaining the invention.

The publications and other materials used herein to illuminate the background of the invention or provide additional details respecting the practice, are incorporated by reference, and for convenience are respectively grouped in the appended List of References.

SUMMARY OF THE INVENTION

The invention consists of several novel solutions to overcome specific problems currently encountered in propagating bamboo. The invention consists of these novel solutions both individually and in combination. The problem areas addressed by the various aspects of the invention include the following:

a) Specific preparation of plants under stage 0 conditions.
b) Use of diseased parts of bamboos as explants for initiation.
c) Reversion of in vivo flowering in vitro.
d) Subculture of flowering parts in vitro as monocultures.
e) Induction of nodule cultures in monocultures of flowering parts.
f) Induction of flowering in vitro by specific combination of chemical and physical parameters.
g) Induction of somatic embryogenesis in adult bamboos without prior organogenesis.
h) Production of synthetic seeds.
i) Dehydration of somatic embryos prior to the production of synthetic seeds.
j) Use of somatic embryos, nodule cultures and shoot tips for cryopreservation using an encapsulation dehydration method.

k) Use of bottomcooling and increased light intensity prior to transplantation.
l) Use of micropropagated plants as micromotherplants for further multiplication.
m) The use of an acetone rinse for sterilization.

The details for performing each of the above are set out in the Examples. The invention teaches how to begin with seeds, vegetative mature seedlings or inflorescences and efficiently micropropagate these on a large or mass scale. A variety of conditions including type of medium, concentrations of auxin and cytokinins, temperature, lighting, humidity and sterilization are disclosed, the use of which results in a high percentage success rate of micropropagation thereby allowing economically viable production of bamboo on a large or mass scale. One or more pathways shown in FIG. 1 are applicable to all species of bamboo including woody tropical, woody temperate and herbaceous species.

DETAILED DESCRIPTION OF THE INVENTION

A large number of papers have been published on tissue culture of bamboos (Rao et al., 1991; Gavinlertvatana, 1992; Saxena and Dhawan, 1994; Zamora, 1994; Nadgauda et al., 1997, for reviews), but in practice, i.e., for large or mass scale propagation of bamboos, these reports are not easily transformed into commercially viable propagation systems. Up to the present day few laboratories have succeeded in developing micropropagation protocols for efficient mass scale propagation.

The difficulties reported or encountered are availability of elite selected material (often restricted to seasonal periods), high incidences of endogenous or surface contaminations and browning of the explants in the first stages, factors related to dormancy or topophysis, hyperhydricity and browning during multiplication stages, the choice of appropriate propagation techniques and problems associated with rooting of tissue cultured plantlets (even in genotypes that root readily in nature, and can be propagated via culm or branch cuttings) (Saxena and Dhawan, 1994). The methods presented below overcome these difficulties and allow much more responsive material for efficient propagation through tissue culture methods, and ultimately efficient yield of viable plants for transplanting.

Figure 1:
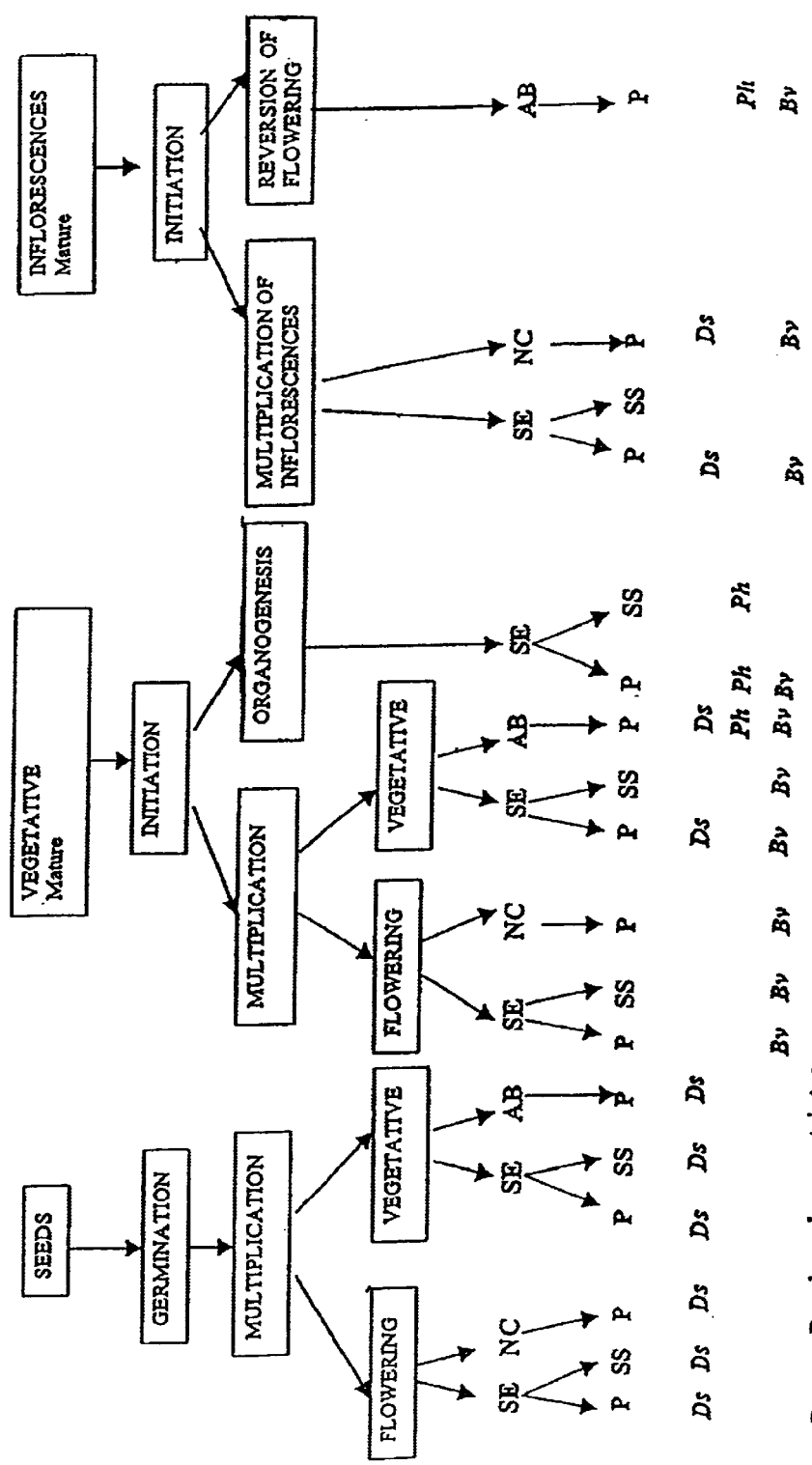
FIG. 1 is a general overview of the many possible pathways from a starting source of material (seeds, vegetative seedlings or inflorescences) through multiplication to eventual plantlets or seeds.

The invention makes available many options for selecting starting materials and the type of product (e.g., plantlet vs. seed) obtained. FIG. 1 illustrates the several pathways available. One may begin with seeds, mature seedlings, mature vegetative plants or inflorescences. These are germinated (seeds) or growth is initiated (seedlings and inflorescences). By selecting appropriate growth conditions (e.g., growth medium, amounts of auxins and cytokinins, temperature, humidity, etc.) one can force the tissue down a desired pathway. For example, looking at FIG. 1, one can begin with tissue from a seedling, have it go through a multiplication step, and then force it along either a flowering or a non-flowering pathway. These in turn can be further cultivated via somatic embryogenesis (SE) or nodule vulture (NC) (flowering pathway) or somatic embryogenesis (SE) or axillary branching (AB) (non-flowering pathway). Finally these somatic embryos, nodules or products of axillary branching can then be forced into pathways of producing either plantlets (P) or synthetic seeds (55). The route chosen will depend on various factors such as the species of bamboo or the scale of production to be obtained. The same explants may also be used for germplasm storage methods. The factors in selecting a desire pathway are discussed in the following paragraphs.

A) Selection of Mother Plants

The first and most fundamental problem is the choice of the mother plants and the plant material used. To optimize the potential and the added value of micropropagation, which in itself is a rather expensive technology compared to other propagation techniques, it is necessary to start with elite selected genotypes while keeping a broad genetic basis. The term elite means the best quality for the purpose desired, e.g., for edible bamboo it is desired to have a high sugar content; for making paper it is desired to have bamboo with long fibers. The term elite is used interchangeably with the term plus. The production of thousands, possibly millions of copies of the original mother plant will determine the ultimate yield of the bamboo plantation. A major added value of micropropagation is that one can select desired phenotypes (elite genotypes for the desired characteristics) and grow those plants.

If plus bamboos are selected, the overall yield of plantations increases dramatically compared to natural populations. On the other hand, when inferior genotypes are selected, the yield will be affected in a negative way in the longer term. An increased yield results from a combination of the selection of elite genotypes and use of improved silvicultural techniques. Selection criteria depend largely upon end use, e.g., fiber length for paper, sugar content for edible bamboo, etc., and not merely upon total mass.

The importance of this cannot be overestimated. The selection of superior clones of bamboos is only in its infancy (Rao and Rao, 1995). Selection currently is mostly based on gross characteristics related mainly to growth and yield. Only in some forest research institutes where bamboos are propagated via seeds will some selection take place before bamboos are planted in the field (Banik, 1995).

B) Seeds vs. Mature Plants as Starting Material

In selecting the mother material for micropropagation or other tissue culture techniques, one basically has two possible sources in bamboos, namely seeds or mature bamboos. Both have advantages and disadvantages.

The advantages of using seeds or seedlings are:
1) The tissue culture techniques for seeds of tropical bamboos are easy to perform. The first report on tissue culture from embryos was by Alexander and Rao (1968), and was followed by numerous other reports (for a review see Zamora, 1994).
2) The seedlings represent new generations. Especially in monocarpic bamboos, the ontogenetic age of the plant will be important to minimize the danger of gregarious flowering in plantations.

The disadvantages of using seeds or seedlings are:
1) Restricted availability and limited storage of seeds. For some bamboos, patches of flowering and seeding bamboos can be found annually somewhere, but for others seeds may be available only in certain years. Seeds of tropical species lose their viability after 2 to 3 months. The availability of seeds of temperate bamboos is even more restricted, although they keep their viability for a longer period.

2) Flowering in tissue culture. Seedlings or seedling derived materials are prone to flowering in vitro induced by as yet unknown mechanisms. Transplanting of these flowering plants may result in the death of the bamboos.
3) The genetic background is unknown. Seedling lots of bamboo are highly heterogeneous not only in the field (McClure, 1966) but also in their response to tissue culture. It is thus very important to select only the best seedlings of good motherplants (which involves at least some observation phase), and to use these for micropropagation.

The unknown genetic background and the heterogeneity in seedling populations are especially important drawbacks. Strategies to circumvent some of the disadvantages of using seeds include:
1) Studies to compare in vitro to in vivo performance, also in the long term.
2) Genetic and molecular studies to assess genetic variability in seedling populations and to develop early assessment methods to evaluate quality at early stages or even at the seed stage.
3) The development of methods for storage of seeds or tissue cultures of seedlings, especially during the period of quality assessment in the field (medium storage or cryopreservation).

Figure 2:
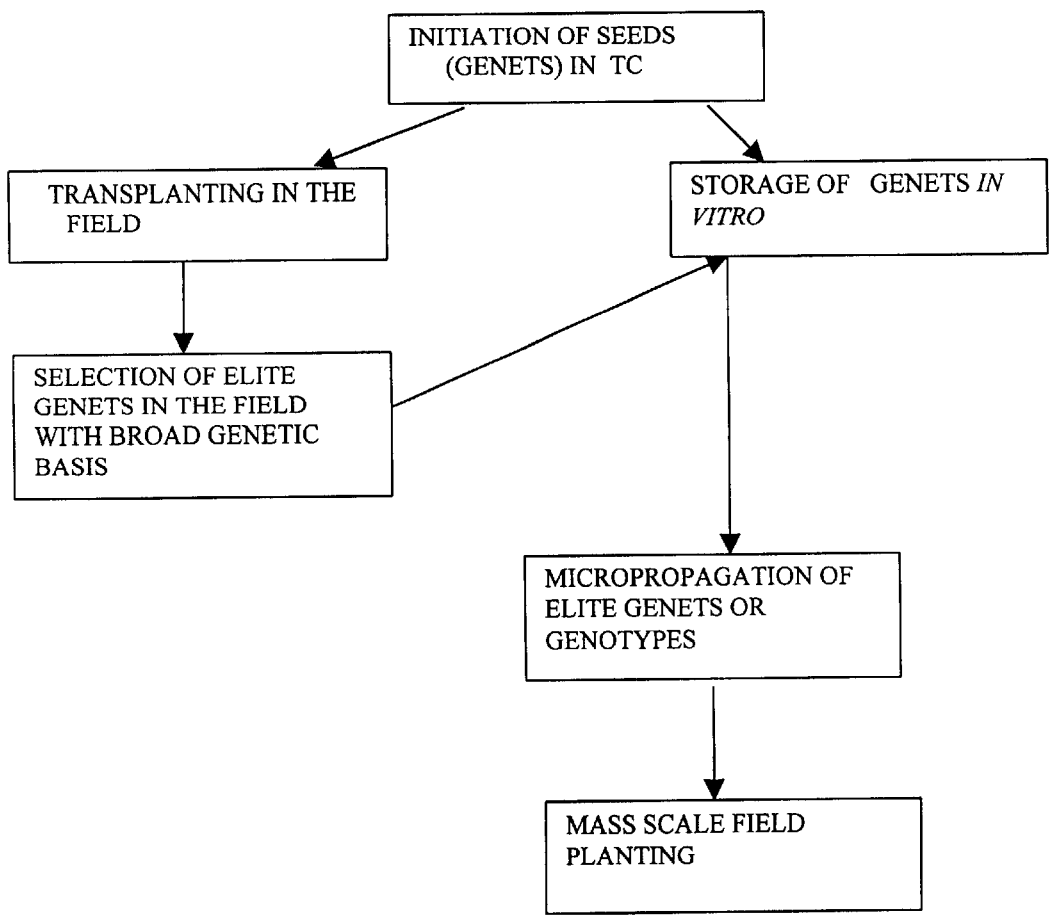
FIG. 2 is a flow diagram of the overall steps in growing bamboo on a large scale by starting with seeds in tissue culture and going through the stage of mass scale field planting.

FIG. 2 is a schematic flow diagram showing the process of selecting material beginning with initiation of seeds in tissue culture (TC) through to the step of mass scale field planting. Once the seeds have been initiated, they can be transplanted in the field where elite genets can be selected. These can be stored in vitro or micropropagated and finally planted on a mass scale. If desired, one can initiate the seeds in tissue culture, then store the seeds or use them for micropropagation and then move into mass scale planting.

The advantages of using adult or mature bamboos are:
1) Direct selection of elite genotypes is possible. In natural populations or seedling populations, plus clones can be identified. As such adult or mature also refers to seedlings which have been established in the field for at least 3 years.
2) Starting material is readily available. The elite clones can be sampled and grown in the vicinity of the laboratory. This also allows circumvention of problems related to seasonal growth as identified (Saxena and Dhawan, 1994).
3) Often adult material is the only material available. For many tropical bamboo species, and for almost all temperate ones, seeds are simply not available.

The main disadvantages of using mature or adult material are:
1) Identification and collection of elite clones is difficult, mainly because of lack of suitable selection criteria and of numerous logistic problems.
2) The development of tissue-culture technology is much more difficult. In comparison with seeds of tropical bamboos, the technology is more difficult, with bottlenecks mainly in the initiation and rooting stages.
3) The ontogenetic age. When adult plants are used in tissue culture some danger exists for flowering as the ontogenetic age of the tissue culture plants equals that of the mother plant.

C) Initiation: Stage I

Initiation of plant material in tissue culture follows surface sterilization. This results in the removal or destruction of surface contaminants living on the surface of leaves, stems, branches or seeds. For many or most bamboos this phase is problematic due to endogenous contamination. Plants growing in the field are not easily sterilized, and most often up to 100% of the inoculated pieces are contaminated, especially in mature bamboos.

As browning of explants occurs very frequently in bamboo tissue culture, resulting in the death of explants after one or a few subcultures (Saxena and Dhawan, 1994), over-sterilization must be avoided in order to minimize browning of explants. The use of fungicides and antibiotics prior to sterilization has been proposed to obtain clean starting material for tissue culture (Hirimburegama and Gamage, 1995), but in practice these components are not successful, and will only postpone problems to later stages.

In recent years it has become clear that many, if not all, plants are contaminated endogenously with microorganisms of different nature. In this emerging field of research increasingly more different microorganisms are detected in plants, exerting all kinds of effects after reintroduction on tissue culture plants. Bamboos are amongst the most 'dirty' plants of all. During the tissue culture process most of these bacteria remain latently present in the plant, and as all tissue culture practitioners know, they can show up at any stage, resulting in significant losses. It has been observed, e.g., that contamination of tissue culture plants or somatic embryos can occur after air transport.

Therefore the art of tissue culture is to make plants grow and suppress the endogenous microorganisms (although microorganisms may be beneficial). Practice has shown that antibiotics have little or no effect in eradicating endogenous microorganisms from tissue culture plants. Rather indexing of cultures as well as careful and continuous observation of culture by operators is necessary. The extra costs of this monitoring, which can mount up to 20% of the operator time, are easily recovered by avoiding contamination in the lab.

D) Choice of the Propagation Method

Tissue culture has provided completely new ways for propagation of bamboos. In bamboos three types of propagation have been described, namely forced axillary branching, organogenesis and somatic embryogenesis.

Organogenesis, or better caulogenesis, has been described in Phyllostachys, Sasa and Bambusa species (Huang et al., 1989). In cultured shoot apices green nodular calli were formed which generated new shoots. These shoots could be rooted and transplanted in the greenhouse. Caulogenesis involves an intermediate callus phase. Caulogenesis was also used as part of a propagation system, namely as pretreatment for the induction of somatic embryogenesis (Woods and Woods, 1994).

Somatic embryogenesis in bamboos has been induced in a range of explants, including seeds and mature embryos (Rao et al., 1985; Yeh and Chang, 1987; Woods et al., 1992), inflorescences (Yeh and Chang, 1986a; Yeh and Chang, 1986b), anthers (Tsay et al., 1990), adult vegetative material (Jullien and Tran Van, 1994; Woods and Woods, 1994) and even in roots (Chang and Lan, 1995).

In seeds or seedlings of tropical bamboos somatic embryogenesis (SE) is induced relatively easily. There is a tremendous clonal variation in propensity for somatic embryogenesis. Despite this variation, a large number of SE derived plants could be transplanted in the field for further evaluation.

In adult bamboos the techniques are much more difficult. While embryogenic-like callus can be obtained, the development and maturation of embryos is the main problem. 2,4-D (2,4-dichlorophenoxyacetic acid) and BA (6-benzyladenine) are both indispensable for induction of SE in *Bambusa multiplex* 'Golden Goddess' (Jullien and Tran Van, 1994), and other bamboos (Woods and Woods, 1994). In the latter study, prior to SE a caulogenic step was necessary.

Forced axillary branching has been induced in seedlings and mature bamboos (for reviews see Gavinlertvatana, 1992; Zamora, 1994; Nadgauda et al., 1997). Only a very limited number of reports deal with forced axillary branching in mature bamboos (Prutpongse and Gavinlertvatana, 1992; Chaturverdi et al., 1993; Saxena and Bhojwani, 1993; Jullien and Tran Van, 1994; Gielis, 1995; Hirimburegama and Gamage, 1995) compared to seedlings.

Major bottlenecks are at the initiation stage, and in the rooting (and consequently the transplantation) stage. Also many problems are encountered at the multiplication stage, mainly quality problems.

E) Comparison of Propagation Methods

One should keep in mind that the ultimate aim of a plant production process in any field of agriculture is the efficient production of high quality plants of genotypes with superior quality. The present invention provides an improvement over the prior art in this respect. Much allied to this is of course the question of scaling up; there is indeed a huge difference between the production of 200 plants in a laboratory and the production of 50,000 plants each of 5 different species (Rao, 1994).

Axillary branching is an efficient method to mass propagate true-to-type plants within a limited time frame. The chance for mutations is minimal contrary to organogenesis or somatic embryogenesis in which an intervening callus phase is needed prior to plant regeneration (Gielis, 1995).

In tropical species initiated from seeds, somatic embryogenesis provides a straightforward method and numerous plants can be produced very rapidly. However, the propensity for somatic embryogenesis is very much genotype related (Saxena and Dhawan, 1994) and due to the methodology somaclonal variation can be expected. However these methods can be used to some extent as part of the tissue culture process, i.e., to generate good propagating cultures. To use somatic embryogenesis in the complete production scheme indeed poses some danger in view of genetic stability, especially since the time needed to feed back information from the field to the laboratory is longer than 5 years.

Major direct advantages of tissue culture in terms of added value in a commercial application are: mass scale production of high quality plants which are easy to transport and to deliver on site, are disease-free and are vigorous growers (e.g., 10,000 plantlets occupy a volume of 2 boxes and can be shipped within 24 hours to any place in the world). Moreover micropropagation is very flexible and rapid upscaling is possible (within 1 year $10^5$ to $10^6$ plants can be produced from any genotype). Such short time frames or large numbers cannot be rivaled by any conventional method.

The present invention circumvents the difficulties outlined above in a number of ways. Most importantly it includes a combination of techniques which all have been developed and optimized on a laboratory scale to achieve the greatest possible success rate as shown in the Examples below. This combined scheme allows any bamboo to be produced successfully via micropropagation, starting from any explant, by selecting a specific pathway. Many species of bamboo can be produced via any or several of the various proposed routes, while other species of bamboo are restricted to only one or a few pathways. These restrictions can either be related to technical difficulties or probable economic drawbacks.

The invention is described in four processes. Process 1 is the conversion of in vivo bamboos into highly responsive propagules in tissue culture. This involves the use of different explants, induction and reversion of flowering. Process 2 involves the induction of somatic embryogenesis in the responsive propagules obtained from process 1 and the encapsulation of somatic embryos to produce synthetic seeds. Process 3 involves the production of quality plants via the different techniques and methods used in processes 1 and 2. Process 4 involves the use of shoot tips, organogenic calli or nodule cultures, obtained in processes 1 and 2, for storage under growth limiting conditions, involving low temperature storage and cryopreservation.

Besides being a combination of techniques, at several instances in the scheme, novel solutions are proposed to tackle specific problems. These novelties are:

a) The specific preparation of the plants under stage 0 conditions.
b) The use of diseased parts of bamboos to be used as explant for initiation.
c) The reversion of in vivo flowering in vitro.
d) The subculture of flowering parts in vitro as monocultures.
e) The induction of nodule cultures in monocultures of flowering parts.
f) The induction of flowering in vitro by specific combination of chemical and physical parameters.
g) The induction of somatic embryogenesis in adult bamboos without prior organogenesis.
h) The production of synthetic seeds.
i) The dehydration of somatic embryos prior to the production of synthetic seeds.
j) The use of somatic embryos, shoot tips or nodule cultures for cryopreservation, using encapsulation dehydration method.
k) The use of variable temperatures to be applied to the bottom of the tissue culture containers and increased light intensity prior to transplantation.
l) The use of micropropagated plants as micromotherplants for further multiplication.
m) The use of an acetone rinse for sterilization.

The present invention is further detailed in the following Examples, which are offered by way of illustration and are not intended to limit the invention in any manner. Standard techniques well known in the art or the techniques specifically described below are utilized.

EXAMPLE 1

Process 1

Stage 0 Conditions

When explants are taken from the field and initiated in tissue culture, the rates of both fungal and microbial infection are very high, most often up to 100%. These rates are very variable during the year and reproducible initiations are not possible. The seemingly uninfected plants have high incidences of browning and mortality during the first subcultures, and infections can be present in a latent stage, and develop later. It is also observed that the duration from initiation to steady propagation cycles in tissue culture is affected in a negative way.

To circumvent this problem motherplants are stored in greenhouse conditions and water is given only on the pot, i.e., water is only given directly on the container in which the plants grow and the plants are not watered by overhead sprinkling. This reduces the surface contamination of the plants considerably. After one month in the greenhouse *Bambusa balcooa* explants were initiated with 100% success, and this could be done repeatedly later on, while when fresh material was collected upon arrival of the plant, 100% of the explants were found contaminated. Due to these sanitary precautions, cultures are initiated at success rates of 80–100% depending on the species. Other sanitary precautions can include the use of pesticides, or biological agents.

Bamboos normally have a very strict developmental pattern, which also affects their response after initiation, most often in a negative way. Moreover, the developmental pattern restricts the availability of good material for repeated initiations. One way to circumvent this problem is to prune the bamboos regularly so that new buds can develop into new shoots. These new shoots can then be used.

The other way is to use plant material that is more responsive. Such plant parts include parts diseased with little leaf disease or witches' broom, or flowering parts. In both cases the axes are shortened, the leaf surface area is reduced considerably and the branching can be very prolific. However, both types of material are especially prone to surface contamination. Little leaf diseased plants or witches' brooms are very often infected by secondary fungi and bacteria, which may be difficult to sterilize. The culture of both types of plants was found to be affected very positively under stage 0 conditions. The development of both witches' brooms/little leaf disease, and flowering can be enhanced and prolonged under these controlled conditions of temperature, water and nutrient application in the greenhouse.

Stage 1: Initiation Stage

The initiation of explants (e.g., seed, vegetative tissue of adult woody bamboo, or reproductive tissue of adult woody bamboo, including diseased portions of plants with witches' broom or little leaf disease) of bamboo into test tubes was found to be highly efficient and reproducible using explants and pretreatments discussed above.

An improved sterilization protocol was found, this being to first rinse the explants with acetone for 3–4 seconds followed by a rinse with sterile water. This treatment prior to sterilization with bleach and rinsing with sterile water can improve the success rates for difficult species. Earlier experiments using ethanol or no alcohol, proved much less efficient.

On the initiation of flowering parts it is possible to manipulate the development by manipulating the water potential. Water potential refers to the work needed to absorb nutrients from the solution. In media with high gel strengths (e.g., high agar concentration), the added chemicals will be less available to the explants, compared to liquid medium. On liquid or semisolid medium (Murashige and Skoog (MS) medium supplemented with cytokinin, e.g., BA from 0.5–100 mg/L) the inflorescences proper mostly ceased development and basal buds (of the pseudospikelet as in, e.g., *Bambusa ventricosa* or Phyllostachys species, or proximal to the semelauctant compound inflorescence in *Fargesia murieliae*) developed into healthy shoots. On the other hand, when cultured on solid medium supplemented with agar (7 g/L), the florets within the spikelets develop and the anthers protrude. Of course, in order to have good propagating cultures, reversion of flowering is preferred. One manner of manipulating water potential is to use Gelrite™ in place of agar. Gelrite™ is a hard medium but has a low water potential. This allows water easily to be taken up by plants. Agar holds water and solutes more strongly and it is harder for plants to get water from agar than from Gelrite™.

In the scientific literature, a number of reports have dealt with the induction of flowering in bamboos. This was done with an agreeable rate of success in some tropical bamboos started from seeds (Nadgauda et al., 1990; Chambers et al., 1991; Rao et al., 1990; Rout and Das, 1994). In mature bamboos only two publications (Prutpongse and Gavinlertvatana, 1992; Gielis, 1995) report the sporadic occurrence of flowering in mature parts in tissue culture. The control over this process would be highly desirable.

Most of the economically important bamboos have pseudospikelets, which are short branches resembling true spikelets in grasses. They terminate in a spikelet, but the basal buds remain dormant and can give rise to new pseudospikelets later. This allows for a continued development of the inflorescence. It is also the basis for the establishment of monocultures of flowering parts, since all these flowering parts can continue to branch indefinitely from the basal buds of the pseudospikelets.

Stage 2: Multiplication

The explants that have been multiplying at a steady rate, typically between 2- and 6-fold every 4 weeks, can be introduced into the multiplication phase. In this stage the plants are subcultured regularly at intervals of 3–5 weeks on an MS medium supplemented with 0.5–10 mg/L of BA and the medium is solidified with Gelritem™ at 1.6–1.7 g/L. Those of skill in the art recognize that there are several different cytokinins and that cytokinins other than BA can be used, not only in this Example but in other Examples of this disclosure. Such cytokinins include, but are not limited to: $N^6(\Delta^2$-isopentenyl) adenine (iP); trans-zeatin (Z); dihydrozeatin ((diH)Z); $N^6$(benzyl)adenine (BAP) and $N^6$(benzyl)adenosine ([9R]BAP). Also included are 6-furfurylaminopurine (kinetin) and thidiazuron (TDZ) (chemical name of N-phenyl-N'-(1,2,3-thidiazol-5-yl)urea; CAS [115-78-6]). There are several other cytokinins including others which are so-called $N^6$ substituted cytokinins. Some of these $N^6$ substituted cytokinins are listed and others are known to those of skill in the art. An $N^6$ substituted cytokinin is a cytokinin with an adenine or adenosine backbone in which the nitrogen at position 6 is substituted by another group.

These plants, or the monocultures of flowering parts including nodule cultures described below, are propagules that are highly efficient for production of plants and for the induction of somatic embryogenesis, especially in adult plants. An alternative route is via organogenesis (Woods and Woods, 1994). While this procedure used explants from the greenhouse or the field, the use of responsive explants in the multiplication stage would provide better material for the induction of organogenesis.

Young shoots can be successfully transferred to multiplication medium or used for other purposes. During multiplication these shoots remain vegetative, but occasionally clusters of pseudospikelets develop at the base of such cultures. It is possible to remove and subculture these as monocultures of inflorescences (or aggregates of pseudospikelets). While in most cultures these structures occur only very sporadically, the frequency of occurrence can be increased by lowering the water potential with the same or higher level of BA (e.g., 2–10 mg/L) or other cytokinin (e.g., kinetin at 2–10 mg/L or thidiazuron at 0.01–0.5 mg/L). Indeed when the Gelrite™ level is decreased from 1.7 g/L to 1.4 or 1.5 g/L in many cultures the frequency of flowering is increased from 1–2% to 10–15% as was observed in *Thyrsostachys siamensis, Dendrocalamus strictus, Bambusa multiplex, Bambusa ventricosa,* and *Phyllostachys species.*

It is important to keep the cytokinin level high (typically between 4 and 10 mg/L for BA). The lowering of the water potential increases the availability of the cytokinins to the plant. At the base of the clusters, pseudospikelets can be found regularly.

In comparison, using seeds of tropical bamboos *Bambusa bambos* and *Dendrocalamus strictus,* induction of flowering was found in up to 70% of the subcultures when cultivated for 3 subsequent subcultures in bioreactors in liquid medium (Nadgauda et al., 1997); their method cannot be extended to mature bamboos.

The possibility of inducing flowering in multiplication at an appreciable level (5–10%) by moderating the water potential thereby increasing the availability of cytokinins, can be exploited by establishing monocultures of inflorescences, which can then be used: a) for multiplication of these monocultures, b) to generate nodule cultures or to induce somatic embryogenesis as explained further, c) as a source of responsive material for induction of somatic embryogenesis, and d) to control the development of inflorescences to produce anthers and gynoecia as a source of material for somatic embryogenesis for production of haploid plants.

Nodule Cultures

Nodule cultures are in effect even more contracted than pseudospikelets in which each nodule is only fractions of a millimeter long. Using monocultures of flowering parts as described above, the frequency of branching can be increased greatly by using BA in a concentration of about 5 mg/L in combination with thidiazuron (TDZ) in a range of 0.05 to 0.5 mg/L. These nodule cultures can then be propagated in further subcultures. In contrast to organogenesis and somatic embryogenesis, nodule cultures do not involve callusing, rather branching is strictly axillary.

Reversion of Flowering

Besides the reversion of flowering in inflorescence parts taken as explants it is also possible to obtain vegetative shoots from monocultures of flowering parts or from nodule cultures. To this aim, the BA level is decreased to typically 0.5–2 mg/L, instead of 2–10 mg/L. TDZ can be present at 0.01–0.05 mg/L or it can be left out.

Development of the Inflorescences

Subculturing of the monocultures of inflorescences is performed as described above. Inflorescences can be used directly to make flowers grow or monocultures of inflorescences or nodule cultures can be grown to produce shoots which then flower. By increasing the water potential drastically in the terminal parts of the pseudospikelets, individual florets start to develop. Anthers and gynoecia develop normally, albeit the sizes are smaller than in vivo organs. The manipulation of this development is accomplished by using agar instead of Gelrite™ to solidify the medium, typically in the range of 6–10 g/L.

EXAMPLE 2

Process 2

A) Induction of Somatic Embryogenesis

Explants prepared in Example 1 are much more efficient for the induction of somatic embryogenesis in mature bamboos than explants taken directly from the greenhouse or the field. The explants used from Example 1 are shoots and branches, or inflorescences.

Somatic embryogenesis can be induced via an intermediate step of organogenesis as described by Woods and Woods (1994). This protocol uses an intervening callus phase prior to induction of somatic embryogenesis. The protocol uses a combination of 2,4-D and a cytokinin.

Somatic embryogenesis has been induced in mature plants in *Bambusa ventricosa, Dendrocalamus strictus* and *B. vulgaris* using only 2,4-D and no cytokinin, but prior to the induction explants were submitted to the same in vitro conditions as described above. This protocol includes first culturing explants in a normal way so that good quality plants in tissue culture are obtained. Pretreatment with cytokinins (either BA or TDZ) allows induction of somatic embryogenesis in parts of these plants without the use of cytokinins in the SE medium (in all other SE studies cytokinins are needed but not so here) and 1–10 mg/L of 2,4-D is used only. The protocol is based on the use of leaves, stems and inflorescences or parts of the inflorescence (anthers and ovaries) of mature bamboos. This protocol (an MS medium and a concentration range of 1–4 mg/L 2,4-D) is reliable and induces somatic embryogenesis in mature plants of *Bambusa vulgaris, Bambusa ventricosa* and *Dendrocalamus strictus* reproducibly. Also in seedlings of *Dendrocalamus giganteus* this protocol produced good somatic embryogenesis. For *D. strictus* a seedling of 7–8 years old was used, which can be considered as a mature plant, and for *D. giganteus* seedlings in vitro were used. The latter are used to compare SE efficiency in mature bamboos and in seedlings.

After 1–2 weeks in 1–10 mg/L 2,4-D in MS medium callus develops on different parts of the explant, mainly on basal parts of the leaf sheaths, in nodal regions and the apical region. After 2–3 months differentiation and embryo-like structures can be observed. For subculture of the calli a selection procedure based on visual selection was developed with positive mass selection towards calli that show embryo development. The embryogenic calli bear much resemblance with the type of embryogenic calli encountered in other grasses and seedlings of bamboo. Embryogenic calli of the three mature genotypes have been successfully subcultured. Subculturing of callus is performed on lower concentrations of 2,4-D, typically 0.2–0.5 mg/L. This is mainly done to avoid somaclonal variation.

The use of cytokinins in the pretreatment medium (i.e, the development of normal plantlets as explained above) was shown to be of vital importance, for both survival of the explants and for the possibility of omitting cytokinins in the induction medium. Without this pretreatment, induction of somatic embryos that can germinate is not possible on 2,4-D only. Moreover, without the proper pretreatment direct somatic embryogenesis is almost impossible in mature bamboos. The pretreatment also affected the germination. The use of BA or TDZ in pretreatment has a clear influence on somatic embryogenesis, on subculture of calli and on germination. Low concentrations of cytokinins in the pretreatment medium yielded a low success rate. BA, TDZ or other cytokinins had to be present in sufficient amounts. The uptake of these cytokinins and their conversion into storage forms (glucosides and ribosides) allows these storage forms to release endogenous and natural cytokinins during SE. TDZ is not a naturally occurring cytokinin, but its use consistently improves the quality of bamboo plantlets. It acts like a combination of auxin and cytokinins.

B) Subculture and Germination of Somatic Embryos

Subculture of embryogenic calli is performed on solid or semi-solid culture medium (MS) supplemented with decreased levels of 2,4-D (in the range of 0.5–1 mg/L) with moderate levels of cytokinins (e.g., 0.2–1.0 mg/L). Cytokinins which can be used include benzyladenine (BA) (including the riboside and glucoside forms), kinetin and TDZ. Subculturing also includes careful selection of embryogenic type of callus, which is generally characterized by being smooth, white and shiny, and containing definite structures.

While germination of embryos was very poor in adult bamboos overall, the use of cytokinins in the pretreatment phase clearly affected germination. In some cultures of *Bambusa ventricosa*, on the callus some abnormal hairy structures and red coloration has been observed. This may be indicative of the development of dormancy in the callus.

So far, research has focused on induction of callus, and subculture of embryogenic calli. Germination of somatic embryos has been obtained in *Bambusa ventricosa, Bambusa vulgaris*, and *D. strictus*. Also in the seedlings of *D. giganteus* plants were successfully recovered. In seedling derived materials, somatic embryogenesis and germination of embryos is more efficient compared to mature material. But in mature material induction of SE is possible reproducibly, given the proper pretreatments.

C) Production of Synthetic Seeds

Somatic embryos can be encapsulated to form synthetic seeds. This requires the steps of detaching somatic embryos from calli by shaken liquid cultures to form single somatic embryos or microclusters of somatic embryos. A microcluster is a group of embryos, e.g., about 2–10 somatic embryos. These cultures are grown in the same medium as for induction (step A of Process 2 described above) but no gelling agent is added. In this way the microclusters of somatic embryos detach from the callus. Next the medium is discarded and the microclusters are encapsulated in alginate beads by dripping, or encapsulated in small blocks or flat wafer blocks by methods known to those skilled in the art.

More specifically, synthetic seeds are prepared using 6% sodium alginate and 100 mM $CaCl_2.2H_2O$. Preparation of somatic embryos for encapsulation is the last stage before encapsulation and is necessary to ensure good quality of the embryos. Instead of using a higher 2,4-D concentration as for induction of somatic embryogenesis, a lower concentration is used (0.05–0.75 mg/L of 2,4-D) or the 2,4-D is substituted by NAA at 0.1–2 mg/L. In addition to these auxins, kinetin is supplied in th range of 0.2–2 mg/L. Encapsulation of somatic embryos is done in alginate beads supplied with $CaCl_2$ for solidification of the capsules or synthetic seeds. Preferably more than one is encapsulated to ensure maximum germination. Usually each synthetic seed contains 2–5 embryos. In addition, the following chemicals are supplied to the encapsulation matrix: NAA at 0.5–2.0 mg/L and kinetin at 0.1–0.8 mg/L; $KH_2PO_4$ at 100–300 mg/L; and chelated iron at 10–40 mg/L of the chelates EDTA or EDDHA. Use of these additional reagents greatly improves the germination of somatic embryos and synthetic seeds.

D) Conservation and Preservation

Somatic embryos, nodule cultures and shoot cultures are subcultured with reduced sugar concentrations (10–20%) and transferred to growth limiting conditions such as low temperatures (e.g. approximately 4° C.) for 1–2 years. Alternatively, the somatic embryos, nodule cultures and shoot tips may be stored in liquid nitrogen with established procedures such as encapsulation, dehydration or vitrification (Ashmore, 1997). Pretreatments as culturing at lower temperatures enhance survival rates after thawing.

EXAMPLE 3

Process 3

A) Rooting of Bamboos

Rooting of adult bamboos remains a major bottleneck to large scale production. Even in genotypes which root well in the soil, rooting of in vitro plants is very difficult, with rooting percentages reported as low as only 30% in preliminary trials on rooting of *Bambusa vulgaris* and var. striata (Yusoff and Ahmad, 1992; Saxena and Dhawan, 1994). Approaches using auxins in several concentrations and combinations have not resulted in significant improvements in rooting. The use of auxin protectors such as phloroglucinol in *Dendrocalamus strictus* (Chaturverdi et al., 1993) and coumarin in *Bambusa tulda* (Saxena and Bhojwani, 1993) have improved the results only slightly.

But such results are obtained on a laboratory scale and are completely inefficient for large scale production, since 50% of rooting success in the lab means 50% of losses in large scale production. If mass propagation of millions of plants is the aim, 98–100% transplanting success is necessary. For comparison, rooting frequencies of 40–70% are generally considered as good in classical branch or culm cuttings (Banik, 1995).

For commercial application, rooting and transplant survival must be between 95% and 100%. Higher losses result in waste of material, time and money, having a direct effect on price and quality, especially in tissue culture which is a costly process. A survey of the literature on bamboo tissue culture reveals that 95–100% rooting is generally achieved only in seedlings or somatic embryo-derived plants.

For a mass scale propagation process it is necessary to be as cost-effective as possible. This means that in the multiplication and scaling up phase, a high multiplication rate should be maintained (typically 4- to 10-fold every 4 weeks depending on the species). Clumps (a clump consists of about 3–5 different plantlets) are subcultured rather than individual plantlets, this being much more efficient since regrowth and multiplication is more rapid and cutting is much easier. The transfer of clumps to rooting medium fails to induce rooting completely. Presumably the high endogenous cytokinin concentrations are responsible for the failure of complete induction. It has been shown that plants can take up a large amount of cytokinins from the medium and convert them into inactive storage forms. These storage forms can later release the free bases, effectively inhibiting rooting. Classically charcoal is used to remove cytokinins from the plants, but in bamboo activated charcoal affects the quality of plants in a very negative manner.

Rooting could be induced on the genotypes tested by placing the plants on a separate medium to improve quality and initiate roots on the plants, or by pouring an extra liquid medium on top of the multiplication medium. The solid rooting medium is MS medium supplemented with sugar (e.g., sucrose, 15–40 g/L), inositol (100 mg/L) and the auxins NAA (naphthalenacetic acid) (0.1–4 mg/L) and indole butyric acid (IBA) (0.5–5 mg/L). The liquid addition medium only contains salt ($KH_2PO_4$ in the range of 150–400 mg/L, preferably 170 mg/L) (for energy) and inositol (100 mg/L) (to stimulate cell division) as well as sucrose (30–40 g/L as a carbon source) and auxins as in the solid medium. The use of liquid medium that is added to the multiplication medium is mainly intended to lower production costs. Indeed, this manipulation avoids a separate subculture of plantlets onto rooting medium. This method has resulted in 95–100% rooting of *Bambusa ventricosa* and *D. strictus* and transplant survival in the greenhouse after 2–4 weeks.

B) Improving the Quality of the Bamboos

Crucial to any propagation scheme is a good propagation, combined with a good quality for transplanting. Most often, plants obtained from the multiplication stage, cannot be transplanted directly to in vivo conditions. They do not form roots and the quality of the leaves is insufficient. In somatic embryogenesis this problem is much less since germination only ensures high quality plants.

For axillary branching it is necessary to improve the quality and induce rooting prior to transplanting. This is done by reducing the amount of cytokinins in this last stage to a concentration of about 0.2–2 mg/L, and by slightly increasing the water potential, once again by increasing the amount of Gelrite™ to 1.7–2.2 g/L.

Quality of plants is also benefitted by moderating physical parameters such as light intensity and relative humidity. In the multiplication stage the light intensity used in the climate chambers is low (1000–1500 lux typically or 30–50 $\mu$mol.s$^{-1}$.m$^{-2}$ PAR (photosynthetically active radiation)) since the cultures are basically heterotrophic using the carbohydrates in the medium as carbon source. In the quality stage (when plants are being brought to the proper physiological conditions for transplanting) the light intensity is preferably increased to 50–90 $\mu$mol.s$^{-1}$.m$^{-2}$, thereby improving the leaf and plant quality.

In the containers the relative humidity is generally very high, close to 100%. The reason is that the plants are grown on shelves, with lamps below so that the bottom of the container is warmer than the top, which is cooled by an air current. Therefore condensation is on the top of the container and the headspace of the container is saturated with moisture. When bottom cooling is applied, the temperature of the bottom is lower than the top, thereby causing water to condense on the bottom. According to the temperature of the bottom the relative humidity can be moderated. The bottom cooling is typically installed as pipes under the containers with water of 17–19° C. (temperature in growth room typically is 22–25° C. when the lights are on). This water is circulated and cooled by a heat exchange device. It has been found that it is better to vary the temperature during growth. An initial higher temperature, e.g., by bottom heating, allows increased rooting after which the cooling is applied to lower the temperature. This decrease in temperature consequently results in decreased relative humidity, e.g., a decrease from 100% to about 80% or lower. The quality of the tissues, including the stomata, is much better at the lower humidity levels as compared to 100% relative humidity seen at the higher temperatures. During the multiplication stage, in which quality is less important, 100% relative humidity can be used.

C) Micromotherplants

Once adapted to in vivo conditions, plants are potted and allowed to develop new shoots and rhizomes. These plants are vigorous and disease free, and can be used as micromotherplants. They can be divided via classical methods of division in the greenhouse thereby increasing the number of plants at lower cost price.

EXAMPLE 4

Bamboos Propagated by Methods of the Invention

FIG. 1 outlines eighteen pathways for generating plants beginning with either seeds, vegetative or mature plants, or inflorescences and then guiding these starting materials down various pathways through flowering or vegetative states (seeds and mature plants) or multiplication of inflorescences or reversion of flowering (inflorescences) and then through somatic embryogenesis, nodule cultures or axillary branching to produce plantlets or synthetic seeds. Although not shown in FIG. 1, the pathways are referred to as pathway number 1, pathway number 2, etc., up to pathway number 18 going from left to right across the bottom of FIG. 1. The methods outlined above have been successfully applied to many different species of bamboo. FIG. 1 shows which pathways have been used successfully for *Dendrocalamus strictus*, *Bambusa ventricosa* and *Phyllostachys* species. Other species of bamboo which have successfully been propagated via at least one of the pathways shown in FIG. 1 using the methods outlined above are shown in Table 1.

TABLE 1

| Temperate Woody Bamboos |
|---|
| *Chimonobambusa marmorea* |
| Fargesia |
| dracocephala |
| murieliae |
| (3 cultivars) |
| nitida (3 cultivars) |
| rufa |
| Phyllostachys |
| aurea |
| aureosulcata |
| (3 cultivars) |
| bissetii |
| edulis |
| "Gracilis" |
| humilis |
| nigra |
| (2 cultivars) |
| vivax |
| Pleioblastus |
| auricomus |
| Variegatus |
| Sasa |
| palmata |
| *Semiarundinaria fastuosa* |
| *Thamnocalamus falconerii* |
| Tropical Woody Bamboos |
| Bambusa |
| multiplex (5 cultivars) |
| balcooa |
| bambos |
| striata |
| ventricosa |
| vulgaris |
| Dendrocalamus |
| asper |
| giganteus |
| membranaceus |
| strictus |
| Dinochloa |
| scandens |
| Otatea |
| acuminata aztecorum |
| Thyrsostachys |
| siamensis |
| Herbaceous Bamboos |
| Lithachne |
| humilis |

EXAMPLE 5

Pathway Number 1

Pathway 1 as shown in FIG. 1 is the process of starting with seeds, going through the steps of germination and multiplication into a flowering stage, and then inducing somatic embryogenesis and finally producing a plantlet. *D. strictus* is one species which can be induced to follow this pathway as shown in FIG. 1. This Example details the methods of taking seeds of *D. giganteus* through pathway 1.

Seeds of *D. giganteus* are collected and initiated in tissue culture after A sterilization procedure consisting of rinsing with acetone for a few seconds, followed by NaOCl treatment of 1% for 10 minutes and finally three rinses with sterile distilled water. During the phase of germination the growth of seedlings is recorded and selection is carried out in terms of branching and height of the shoots. From these the top 20% genotypes are taken further in tissue culture.

One specimen of each genotype is transplanted as rapidly as possible to monitor growth under field conditions.

Subculture periods are fixed at 5 weeks, and the medium used consists of a general MS medium, solidified with Gelrite™ and supplemented with BA at 5 mg/L. When the multiplication reaches a steady state over time, the plants enter the production stage and the BA content is lowered to between 0.5 and 2 mg/L.

In the production stage, flowering can be observed frequently when either BA is kept at high levels (e.g., 5 mg/L), or when Gelrite™ concentrations are decreased, e.g., to 1.5–1.6 g/L, or both, resulting in increased hyperhydricity. These inflorescences are then used to induce somatic embryogenesis. Because of the prior in vitro stage, 2,4-D alone at concentrations of 2–4 mg/L suffices to induce SE.

Subculture of callus and regeneration of plants is greatly benefitted by the addition of kinetin (1 mg/L) and lowering of 2,4-D to 0.5 mg/L in the subculture stage, and total omission of 2,4-D from the regeneration medium.

EXAMPLE 6

Pathway Number 9

Pathway 9 as shown in FIG. 1 is the process of starting with mature vegetative plants, going through the steps of initiation and multiplication into a flowering stage, and then inducing nodule cultures and finally producing a plantlet. *B. ventricosa* is one species which can be induced to follow this pathway as shown in FIG. 1. This Example details the methods of taking *B. ventricosa* through pathway 9.

When plants of *Bambusa ventricosa* are kept under Stage 0 conditions the sterilization procedure as in Example 5 ensures 100% success of initiation. Subculturing of plants can be done at BA 1–2 mg/L.

When cultured at hyperhydricity inducing conditions (higher BA or cytokinin concentrations, e.g., BA at 6 mg/L) induction of flowering can occur. These inflorescences are then subcultured again on Gelrite™ medium supplemented with BA at 4 mg/L, thereby forming balls of pseudospikelets, and regular subculture of these pseudospikelet balls can maintain these flowering states indefinitely. The pseudospikelets are typically between 1 and 2 cm long. In this state individual florets do not develop.

If however BA is raised to about 8 mg/L and TDZ is added at 0.5 mg/L, branching becomes more profuse and the size of the pseudospikelets reduces to 1 or 2 mm only. This then is a nodule culture, in which there is only axillary branching as in the pseudospikelet balls. These nodule cultures resemble very small clumps of plants that can be multiplied further.

Plant regeneration is done by lowering BA concentration to 2 mg/L and omission of TDZ so that we again have pseudospikelet balls, from which one can regenerate plants. The major advantage of nodule cultures is the ultimate reduction of size of the propagules. Typically one small nodule of 5 mm across can hold up to 50 plants. The main advantage is that branching is axillary only, without intervening callus formation.

EXAMPLE 7

Pathway Number 12

Pathway 12 as shown in FIG. 1 is the process of starting with mature vegetative plants, going through the steps of initiation and multiplication into a vegetative stage, and then inducing axillary branching and finally producing a plantlet. *D. strictus*, a number of *Phyllostachys* species, and *B. ventricosa* can be induced to follow this pathway as shown in FIG. 1. This Example details the methods of taking mature *Phyllostachys aurea* through pathway 12.

Plants of *Phyllostachys aurea* are selected with symptoms of witches' broom or little leaf disease. These plants are kept under Stage 0 conditions and are characterized by profuse branching of slender and long shoots, with strongly reduced leaf blades. The procedure for sterilization is the same as in Example 5. Once the new cultures are established, they are further multiplied on media with BA at 5 mg/L with the addition of a small amount of TDZ (0.1 mg/L).

In the production line the concentrations of the cytokinins are balanced and equilibrated towards a high multiplication rate, i.e., the cytokinin concentration is made as high as possible to achieve maximum multiplication while having only a small effect upon the quality. Towards the transplanting stage however, the cytokinins are used in lesser concentrations, typically 1–2 mg/L BA or similar $N^6$ substituted ones. The addition of liquid medium (20 mL per culture container) supplemented with sucrose at 30 g/L, potassium dihydrogen phosphate at 170 mg/L and NAA at 0.2 mg/L promotes the induction of rooting.

EXAMPLE 8

Pathway Number 14

Pathway 14 as shown in FIG. 1 is the process of starting with mature vegetative plants, going through the steps of initiation and organogenesis, and then inducing somatic embryogenesis and finally producing synthetic seeds. Species of Phyllostachys can be induced to follow this pathway as shown in FIG. 1.

Basically, somatic embryos are obtained as described in U.S. Pat. No. 5,334,530, via an intermediate step of organogenesis. The embryogenic clusters are further multiplied in a liquid suspension culture. Instead of using a higher 2,4-D concentration as for induction of somatic embryogenesis, a lower concentration is used (0.05–0.75 mg/L 2,4-D), or the 2,4-D is substituted by NAA at 0.1–2 mg/L. In addition to these auxins, kinetin is supplied in the range of 0.2–2 mg/L.

The synthetic seeds are prepared using 6% of sodium alginate and 100 mM $CaCl_2 2H_2O$. More than one, preferably 2–5 embryos are encapsulated to ensure maximum germination. In addition, the following chemicals are supplied to the encapsulation matrix: 1) NAA (0.5–2 mg/L) and kinetin (0.1–0.8 mg/L); 2) $KH_2PO_4$ (100–300 mg/L) and 3) chelated iron (10–40 of the chelates EDTA or EDDHA. These additions greatly improve germination of somatic embryos and synthetic seeds.

EXAMPLE 9

Pathway Number 17

Pathway 17 as shown in FIG. 1 is the process of starting with inflorescences, going through the steps of initiation and multiplication of inflorescences, and then inducing nodule cultures and finally producing a plantlet. *D. strictus* and *B. ventricosa* can be induced to follow this pathway as shown in FIG. 1. This Example details the methods of taking inflorescences of *B. ventricosa* through pathway 17.

Flowering branches of *Bambusa ventricosa* are used to initiate in vitro cultures. Stage 0 conditions and sterilization procedure are the same as in the preceding Examples.

Subculture of the inflorescences on high BA as in pathway 9 (see Example 6) results in balls of pseudospikelets. For nodule cultures and plantlet regeneration, the process is the same as for pathway 9 (see Example 6).

EXAMPLE 10

Pathway Number 18

Pathway 18 as shown in FIG. 1 is the process of starting with inflorescences, going through the steps of initiation and reversion of flowering, and then inducing axillary branching and finally producing a plantlet. Species of Phyllostachys and *B. ventricosa* can be induced to follow this pathway as shown in FIG. 1. This Example details the methods of taking inflorescences of *Fargesia murieliae* through pathway 18.

When inflorescences of *Fargesia murieliae* are initiated on liquid medium supplemented with BA at 10 mg/L, the dormant buds proximal to the partial inflorescence can develop into so-called innovation shoots with normal vegetative growth. This is reversion of flowering. Once this reversion of flowering is obtained, the vegetative shoots can be cultured as regular AB cultures (see pathway 12 as illustrated in Example 7).

The semelauctant (i.e., flowering at once) inflorescence of *Fargesia murieliae*, consists of a short paracladial zone of true spikelets. This zone is subtended by the last 'normal leaf' of the flowering branch. Distal to this zone are dormant buds on the proximal internodes. These buds can develop into new flowering branches in normal development (supplementing zone), or to vegetative shoots (innovation shoots) under well defined conditions, such as tissue culture conditions.

In contrast, inflorescences with pseudospikelets, such as in *Bambusa, Dendrocalamus* and Phyllostachys, have a different mode of development. Unlike in true spikelets, in which all buds develop into florets, in pseudospikelets the proximal buds remain dormant, and can develop into new pseudospikelets, so that the supplementing zone is in the pseudospikelet proper.

It must be noted that neither FIG. 1 nor the Examples are meant to be limiting. Species of bamboo other than those shown in FIG. 1 or those used in the Examples can similarly be successfully propagated via the pathways shown in FIG. 1.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Alexander M P and Rao T C (1968). *Current Science* 37:415.

Arya I D and Arya S (1996). "Micropropagation protocol for exotic edible bamboo (*Dendrocalamus asper*)." Technical Bulletin of Tropical Forest Research Institute (Jabalpur, M P, India), 13 pp.

Ashmore S E (1997). "Status Report on the Development and Application of In Vitro Techniques for the Conservation and Use of Plant Genetic Resources." Ed. F. Engelman (Intl. Plant Genetic Resources Institute, Rome, Italy).

Banik R L (1995). "Selection criteria and population enhancement of priority bamboos." In: J. T. Williams, I. V. Ramanuja Rao, A. N. Rao (Eds) *Genetic enhancement of bamboo and rattan* (New Delhi: INBAR Technical Report No. 7), 99–110.

Chambers S M, et al. (1991). *Plant, Cell, Tissue and Organ Culture* 27:45–48.

Chang W C and Lan T H (1995). *J. Plant Physiol.* 145:535–538.

Chaturverdi H C, et al. (1993). *Plant Science* 91:97–101.

Gavinlertvatana P (1992). *Forest News* 6:1–16.

Gielis J (1995). *European Bamboo Society Journal*, May 6, pp. 27–39.

Hirimburegama K and Gamage N (1995). *J. Horticultural Science* 70:469–475.

Huang L C, et al. (1989). *Environmental and Experimental Botany* 29:307–315.

Huang L C and Huang B L (1992). "Bamboo tissue culture" In: Chiang C H, Wang Y N (Eds.) *Proceedings of the 1992 Joint International Symposium on Air Pollution, Soil Microbiology and Biotechnology in Forestry*, pp. 293–304.

Huang L C and Huang B L (1995). *Plant, Cell, Tissue and Organ Culture* 42:109–111.

Jullien F and Tran Van T (1994). *Plant Science* 98:199–207.

McClure F A (1966). *The Bamboos—A fresh perspective.* (Harvard University Press, Cambridge, Mass.).

Nadgauda R S, et al. (1990). *Nature* 344:335–336.

Nadgauda R S, et al. (1997). "Application of in vitro techniques for bamboo improvement" In: Chapman G (Ed.) *The Bamboos* (Academic Press, London), pp. 163–177.

Prutpongse P and Gavinlertvatana P (1992). *HortScience* 27:453–454.

Rao I V R (1994). "Delivery systems for planting materials: requirements and approaches"*Constraints to production of bamboo and rattan*: INBAR Technical Report 5 (Delhi), pp. 143–158.

Rao I V R, et al. (1985). *Plant Cell Reports* 4:191–194.

Rao I V R, et al. (1990). "Tissue culture approaches to the mass propagation and genetic improvement of bamboos. In: Rao IVR, Gnanaharan R, Sastry C B (Eds.) *Bamboos Current Research* (KFRI/IDRC, Delhi), pp. 151–158.

Rao I V R, et al. (1991). "Propagation of bamboo and rattan through tissue culture" INBAR (Delhi:IDRC), 60 pp.

Rao A N and Rao V R (1995). "Patterns of variation in bamboos" In: J T Williams, I V Ramanuja Rao, A N Rao (Eds.) *Genetic enhancement of bamboo and rattan* (New Delhi: INBAR Technical Report No. 7), pp. 43–60.

Rout G R and Das P (1994). *Plant Cell Reports* 13:683–686.

Saxena S and Bhojwani S S (1993). *In Vitro Cellular and Developmental Biology* 29P:135–142.

Saxena S and Dhawan V (1994). "Micropropagation research in south Asia. Constraints to production of bamboo and rattan." INBAR Technical Report 5 (Delhi), pp. 101–113.

Tsay H S, et al. (1990). *Plant Cell Reports* 9:349–351.

Woods S H, et al. (1992). *Plant Cell Reports* 11:257–261.

Woods S H and Woods J E (1994). U.S. Pat. No. 5,334,530.

Yeh M L and Chang W C (1986a). *Plant Cell Reports* 5:409–411.

Yeh M L and Chang W C (1986b). *Theoretical and Applied Genetics* 7:161–167.

Yeh M L and Chang W C (1987). *Plant Science* 51:93–96.

Yusoff A M and Ahmad D (1992). "Production of bamboo propagules via tissue culture for large scale planting programs."*Proceedings of the National Bamboo Seminar* 1. Forest Research Institute Malaysia FRIM, Kuala Lumpur, pp. 64–72.

Zamora A B (1994). "Review of micropropagation research on bamboos." Constraints to production of bamboo and rattan. INBAR Technical Report No. 5 (Delhi), pp. 45–100.

What is claimed is:

1. A method for preparing material for micropropagation of bamboo or storage of bamboo germplasm comprising the steps of:
   a) growing bamboo plants under greenhouse conditions;
   b) initiating vegetative or reproductive shoots in said bamboo plants in vivo; and
   c) multiplying said vegetative or reproductive shoots in tissue culture via direct shoot multiplication.

2. A method for micropropagating bamboo plants comprising steps (a)–(c) of claim 1 and further comprising the steps of:
   d) inducing nodule cultures or axillary branching in said shoots of step (c) wherein said inducing results in formation of a plantlet;
   e) placing said plantlets on rooting medium;
   f) growing aid plantlets under conditions of high light intensity and bottom cooling; and
   g) transferring said plantlets to conventional growing conditions.

3. A method for preparing germplasm comprising steps (a)–(c) of claim 1 and further
   comprising he steps of:
   d) inducing somatic embryogenesis to produce embryos; and
   e) producing synthetic seeds comprising said embryos.

4. The method of claim 1 further comprising the steps of:
   d) growing aid bamboo plants in containers; and
   e) watering aid bamboo plants directly on said containers to minimize contamination.

5. The method of claim 1 wherein said vegetative or reproductive shoots are grown from seed, vegetative tissue of adult woody bamboo, or reproductive tissue of adult woody bamboo.

6. The method of claim 5 wherein said vegetative shoots are selected from healthy or diseased plants.

7. The method of claim 6 wherein said diseased plant comprises witches' broom or little leaf disease.

8. The method of claim 1 further comprising a step of rinsing said shoots with acetone.

9. The method of claim 1 wherein said multiplying via direct shoot multiplication in tissue culture comprises growing said shoots in a tissue culture medium comprising cytokinin.

10. The method of claim 9 wherein said cytokinin is selected from the group cons sting of $N^6(\Delta^2$-isopentenyl) adenine; trans-zeatin; dihydrozeatin; $N^6$(benzyl)adenine; $N^6$(benzyl)adenosine; 6-fufurylaminopurine; and thidiazuron.

11. A method of multiplying bamboo explants via direct shoot multiplication wherein said method comprises subculturing said explants on MS medium supplemented with one or more auxins and one or more cytokinins, wherein said cytokinins are selected from the group consisting of $N^6(\Delta^2$-isopentenyl) adenine; trans-zeatin; dihydrozeatin; $N^6$(benzyl)adenine; $N^6$(benzyl)adenosine; 6-furfurylaminopurine; and thidiazuron, and wherein said medium is solidified with a gellan-gum gelling agent.

12. The method of claim 11 wherein said cytokinins other than thidiazuron are pr sent at 0.5–10 mg/L and wherein thidiazuron is present at 0.01–0.5 mg/L.

13. The method of claim 11 wherein said gellan-gum gelling agent is present at 1.6–1.7 g/L.

14. A method of inducing flowering in adult bamboo in tissue culture at a level of 50–10% wherein said method comprises growing said bamboo on culture medium solidified with a gellan-gum gelling agent at 1–2 g/L and containing one or more cytokinins selected from the group consisting of $N^6(\Delta^2$-isopentenyl)adenine at 2–10 mg/L; trans-zeatin at 2–10 mg/L; dihydrozeatin at 2–10 mgIL; $N^6$(benzyl)adenine at 2–10 mg/L; $N^6$(benzyl)adenosine at 2–10 mg/L; 6-furfurylaminopurine at 2–10 mg/L; and thidiazuron at 0.01–0.5 g/L, thereby inducing flowering.

15. The method of claim 14 wherein said gellan-gum gelling agent is present at 1.4–1.5 g/L.

16. A method of preparing nodule cultures of bamboo comprising placing monocultures of flowering parts of bamboo in culture in the presence of an $N^6$ substituted cytokinin at a concentration of about 2–10 mg/L and in the presence of thidiazuron at a concentration of 0.01–0.5 mg/L, thereby preparing nodule cultures of bamboo.

17. The method of claim 16 wherein said $N^6$ substituted cytokinin is selected from the group cons sting of $N^6(\Delta^2$-isopentenyl) adenine; $N^6$(benzyl)adenine; and $N^6$(benzyl) adenosine.

18. A method to reverse flowering of inflorescence of bamboo in tissue culture wherein said method comprises culturing said inflorescence in the presence of $N^6$ substituted cytokinin at 0.5–2 mg/L.

19. The method of claim 18 wherein said at least one $N^6$ substituted cytokinin is selected from the group con sting of $N^6(\Delta^2$-isopentenyl) adenine; $N^6$(benzyl)adenine; and $N^6$(benzyl)adenosine.

20. A method of obtaining vegetative shoots from monocultures of flowering parts of bamboo via direct shoot multiplication comprising culturing said monocultures f flowering parts of bamboo in medium in the presence of at least one $N^6$ substituted cytokinins at 0.5–2 mg/L, thereby obtaining vegetative shoots.

21. The method of claim 20 wherein said at least one $N^6$ substituted cytokinin is selected from the group con sting of $N^6(\Delta^2$-isopentenyl) adenine; $N^6$(benzyl)adenine; and $N^6$(benzyl)adenosine.

22. A method to increase development of individual florets in bamboo which have been grown via direct shoot multiplication said method comprising growing monocultures of inflorescences on a solid medium wherein said solid medium comprises agar approximately at a concentration of 7–10 g/L.

23. A method to induce rooting of bamboo shoots which have been grown via direct shoot multiplication wherein said method comprises placing said shoots in a medium containing auxins at a concentration of 0.1–5 mg/L.

24. The method of claim 23 wherein said auxins are selected from naphthalenacetic acid (NAA) or indole butyric acid (IBA).

25. A method to induce rooting of bamboo plants which have been grown on a multiplication medium via direct shoot multiplication wherein said method comprises adding additional medium on top of said multiplication medium wherein said additional medium comprises auxins at a concentration of 0.1–5 mg/L.

26. The method of claim 25 wherein said auxins are selected from NAA or IBA.

27. The method of claim 25 wherein said additional medium further comprises $KH_2PO_4$, inositol and a sugar.

28. A method of obtaining high quality bamboo plants from tissue culture via direct shoot multiplication wherein said method comprises growing tissue in a tissue culture medium within a tissue culture container, said medium comprising 1.7–2 g/L gellan-gum gelling agent, and at least one cytokinin selected from the group consisting of $N^6(\Delta^2$-isopentenyl) adenine; trans-zeatin; dihydrozeatin; $N^6$(benzyl)adenine; $N^6$(benzyl)adenosine; 6-furfurylaminopurine; and thidiazuron, wherein said cytokinins other than thidiazuron are present at 0.5–10 mg/L and wherein thidiazuron is present at 0.01–0.5 mg/L.

29. The method of claim 28, further comprising growing said tissue during a multiplication stage in the presence of light at an intensity of 30–50 $\mu$mol.s$^{-2}$ PAR.

30. The method of claim 29 further comprising growing said tissue at a light intensity of 50–90 $\mu$mol.s$^{-1}$m$^{-2}$ during a quality stage of culturing.

31. The method of claim 28, further comprising bottom cooling of tissue culture containers.

32. The method of claim 31 wherein said bottom cooling is performed by placing said tissue culture containers on a surface at 17–19° C.

33. The method of claim 31 wherein said bottom cooling is performed by circulating a liquid with a temperature of about 17–19° C. beneath said tissue culture containers.

34. A method of obtaining vegetative shoots from nodule cultures of bamboo comprising culturing said nodule cultures of bamboo in medium in the presence of $N^6$ substitute cytokinins at 0.5–2 mg/L, thereby obtaining vegetative shoots.

* * * * *